United States Patent [19]
Gordon et al.

[11] 4,237,796
[45] Dec. 9, 1980

[54] REVOLVING EXAMINATION TABLE APPARATUS

[75] Inventors: Michael D. Gordon; Hollis D. Baker, both of Derby, Kans.

[73] Assignee: Ro-Ta Development Company, Derby, Kans.

[21] Appl. No.: 945,587

[22] Filed: Sep. 25, 1978

[51] Int. Cl.³ .................... A47B 11/00; A47B 81/00
[52] U.S. Cl. .................................. 108/22; 108/20; 108/103; 108/139; 312/239
[58] Field of Search ................ 108/20, 21, 22, 103, 108/139; 248/349; 104/35, 48; 211/1.5; 312/239, 252, 197, 59, 125, 135; 351/38

[56] References Cited

U.S. PATENT DOCUMENTS

| | | | |
|---|---|---|---|
| Re. 29,767 | 9/1978 | Futch | 108/22 |
| 329,992 | 11/1885 | Appell | 312/239 X |
| 1,259,653 | 3/1918 | Masterman | 312/239 X |
| 2,560,001 | 7/1951 | Scholfield | 312/239 X |
| 2,631,909 | 3/1953 | Williams | 108/139 X |
| 3,119,394 | 1/1964 | Knittel | 312/59 X |
| 3,361,508 | 1/1968 | Chassevent | 312/239 |
| 3,383,147 | 5/1968 | Prouly et al. | 211/1.5 X |
| 3,572,913 | 3/1971 | Korb | 351/38 |
| 3,647,287 | 3/1972 | Schwind | 108/139 X |
| 3,710,477 | 1/1973 | Frawley | 312/97.1 |
| 4,114,541 | 9/1978 | Weddendorf | 108/20 |

FOREIGN PATENT DOCUMENTS 1020452  11/1952  France ........................ 351/38

*Primary Examiner*—James T. McCall
*Attorney, Agent, or Firm*—Phillip A. Rein

[57] ABSTRACT

This invention is a revolving examination table apparatus to be used by, for example, optometrists during eye examination to place a desired instrument between the patient and the doctor. More particularly, the table apparatus includes (1) a main, circular support base assembly; (2) a revolving table top assembly rotatably mounted on the support base assembly; and (3) an electrical control and drive assembly operable to control rotation of the revolving table top assembly. A central portion of the support base assembly and the revolving table top assembly is cut out to receive a chair and person (optometrist) therein while the patient sits opposite therefrom with the table apparatus therebetween. The electrical control and drive assembly operates to (1) rotate the table top assembly to one of seven stations and stop automatically; (2) supply electrical power to each station when in the usage position to an electrical receptacle to power an instrument at that station; (3) control direction of table top assembly rotation; (4) control speed of subject rotation; and (5) provide an override switch to by-pass a station, if so desired.

6 Claims, 10 Drawing Figures

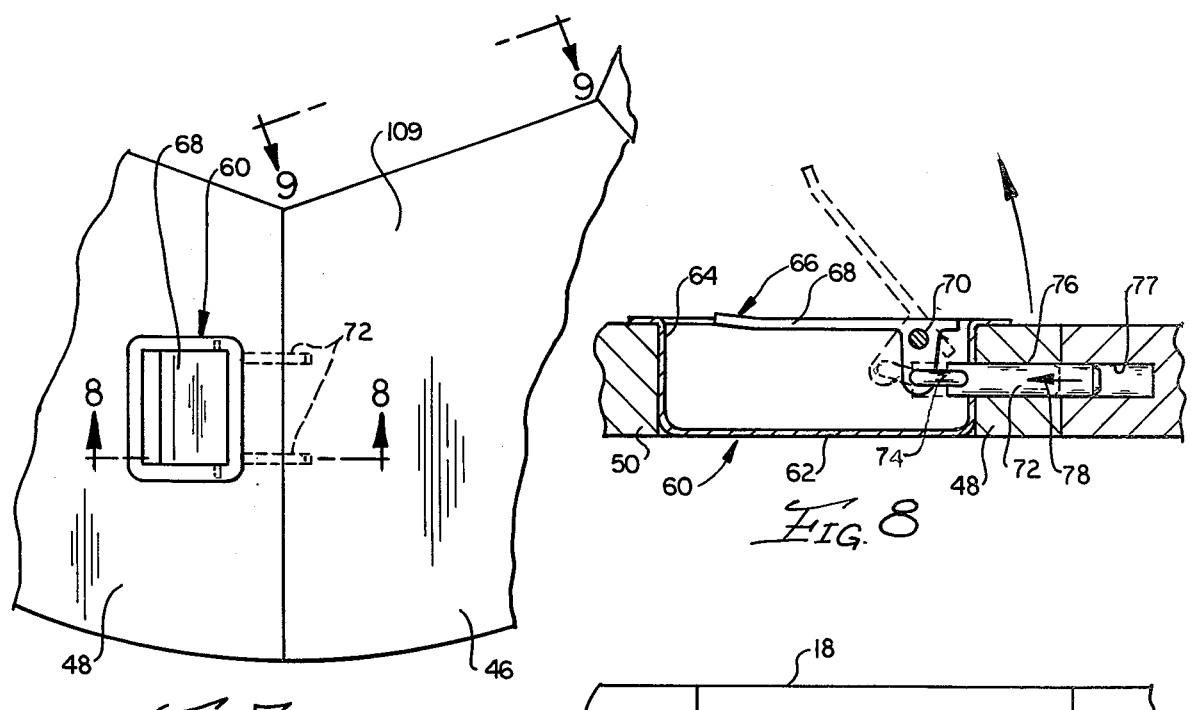
Fig. 7
Fig. 8
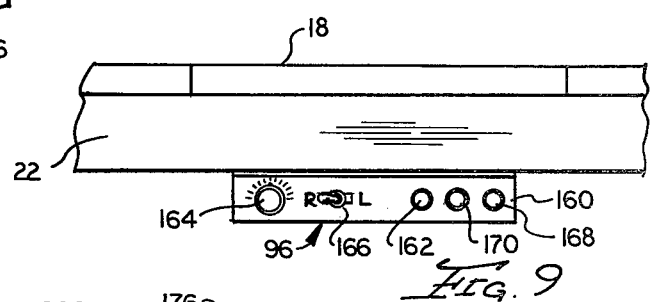
Fig. 9
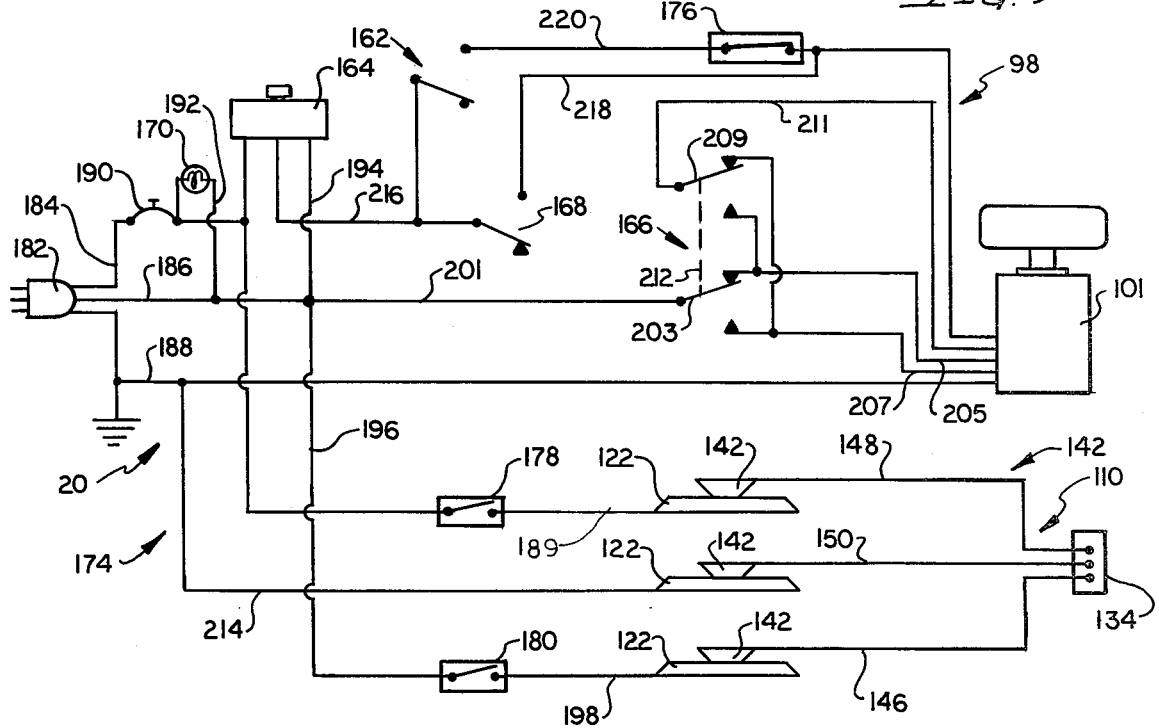
Fig. 10

REVOLVING EXAMINATION TABLE APPARATUS

PRIOR ART

A search of the prior art revealed the following patents that would be of interest relative to our invention: 1,020,452 (France) U.S. Pat. No. 3,647,287 1,104,990 (France) U.S. Pat. Nos. 2,902,471 2,529,581 3,004,571 3,142,269.

The two French patents teach use of a rotating table to bring instruments into the reach of a doctor but differ considerable in overall appearance and usage of applicant's invention.

The most pertinent reference is the Schwind patent which teaches the function of a revolving work surface for an ophthalmologist. However, Schwind fails to provide electrical outlets or a 360 degree table top surface as presented in this application.

PREFERRED EMBODIMENT OF THE INVENTION

The revolving examination table apparatus includes (1) a main support base assembly; (2) a revolving table top assembly mounted on the main support base assembly; and (3) an electrical control and drive assembly operable to drive and control operation of the revolving table top assembly and selectivity provide electrical power to electrical receptacles. The main support base assembly includes a base table top member supported on a plurality of support leg members and having a plurality of spaced roller assemblies secured to an upper surface of the table top member. The table top member is of a ring shape having an open central portion and a section of the table top member cut out to permit access to the open central portion. The revolving table top assembly includes a main table top assembly having a support track assembly connected thereto. The main table top assembly includes six (6) interconnected rigid instrument table sections and a pivotal entrance table section to gain access to the open central portion. Similarly, the main table top assembly is of ring shape having a central open portion but a continuous top working surface when the entrance table section is in the closed, latched, horizontal position. The support track assembly is connected to an undersurface of the main table top assembly and rides on the spaced roller assemblies of the basic table top member to permit rotation of the main table top assembly. The electrical control and drive assembly includes (1) a table drive assembly operably connected to the main table top assembly; (2) a power contact assembly; (3) a control panel assembly and (4) an electrical control assembly. The table drive assembly includes a drive motor member connected through a gear box to a drive wheel member. The drive wheel member contacts the support track assembly to selectively rotate the main table top assembly. The power assembly includes (1) a stationary power contact assembly secured to the basic table top member at a home base station; and (2) a receptacle power contact assembly at each of the six (6) instrument table sections. Each receptacle power contact assembly includes an electrical power outlet receptacle which is energized only when reaching the home base station by the stationary power contact assembly. The control panel assembly includes (1) an on-off switch to initiate power to rotate the main table top assembly; (2) a rheostat swich to control speed of subject rotation; (3) a table rotation switch to select direction of rotation of the main table top assembly; (4) a power indicator light; and (5) an override switch is operable to by-pass one or more working stations on initiating rotation of the main table top assembly. The electrical control assembly provides power to (1) the drive motor member; (2) the main power assembly; (3) the control panel assembly; and (4) includes a control switch assembly. The control switch assembly operates to automatically stop rotation of the main table top assembly at the home base working station and provides electrical power to the receptacle power contact assembly at the subject working station.

OBJECTS OF THE INVENTION

One object of this invention is to provide a revolving examination table apparatus having a circular table with a central opening to receive an optometrist therein with a revolving table top assembly to selectively move stations with examining equipment thereon to the home base working station between the optometrist and his patient.

Another object of this invention is to provide a revolving examination table apparatus of a circular ring shape with a revolving table top assembly that is rotatable and automatically stopped at a desired position.

Still, another object of this invention is to provide a revolving examination table apparatus of a circular ring shape operable to be selectively rotated to a home base working station and to provide electrical power to a receptacle member at this position to power an examining instrument.

One other object of this invention is to provide a revolving examination table apparatus having a revolving table top assembly that is controlled by an electrical control and drive assembly in order to (1) control direction of rotation; (2) control speed of rotation; (3) automatically rotate the next station to the home base working station; and (4) by-pass the automatic controls and move any station to the home base working station.

Still, one further object of this invention is to provide a revolving examination table apparatus that is sturdy in construction, attractive in appearance, reliable in operation, and easy to use.

Various other objects, advantages and features of the invention will become apparent to those skilled in the art from the following discussion, taken in conjunction with the accompanying drawings, in which:

FIG. 7 is a fragmentary top plan view of a portion of the revolving table top assembly of this invention illustrating a latch assembly;

FIG. 8 is an enlarged sectional view taken along line 8—8 in FIG. 7;

FIG. 9 is a fragmentary plan view taken along line 9—9 in FIG. 7; and

FIG. 10 is an electrical schematic of an electrical control and drive assembly of this invention.

Figure 1:
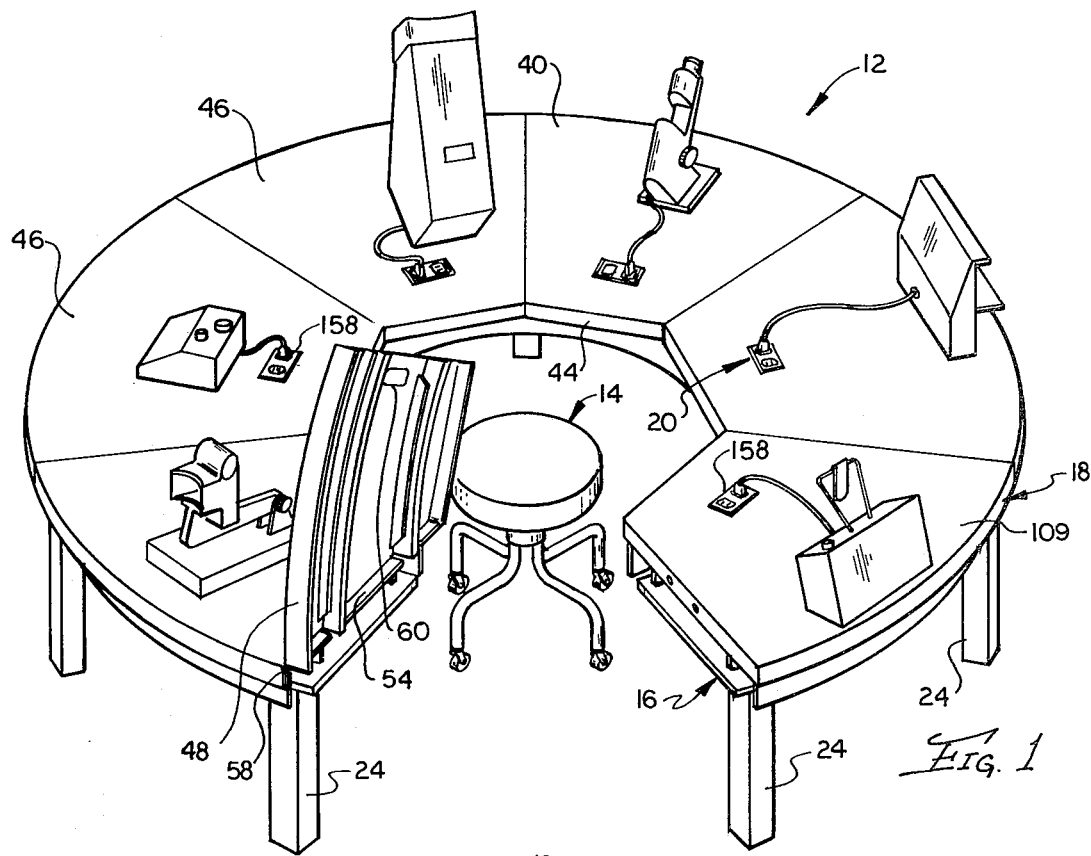
FIG. 1 is a perspective view of the revolving examination table apparatus of this invention illustrating an entrance table section in the open position.

The following is a discussion and description of preferred specific embodiments of the new revolving examination table apparatus of this invention, such being made with reference to the drawings, whereupon the same reference numerals are used to indicate the same or similar parts and/or structure. It is to be understood that such discussion and description is not to unduly limit the scope of the invention.

DESCRIPTION OF THE INVENTION

Referring to the drawings in detail and in particular to FIG. 1, a revolving examination table apparatus of this invention, indicated generally at 12, is shown associated with a conventional optometrist examining stool 14. The revolving examination table apparatus 12 includes a main support base assembly 16; a revolving table top assembly 18 mounted on the main support base assembly 16; and an electrical control and drive assembly 20 operable to rotate the revolving table top assembly 18 in a manner to be explained.

The main support base assembly 16 includes a basic table top member 22 supported on spaced support leg members 24 and having spaced roller assemblies 26 secured to an upper support surface 28 of the basic table top member 22.

Figure 6:
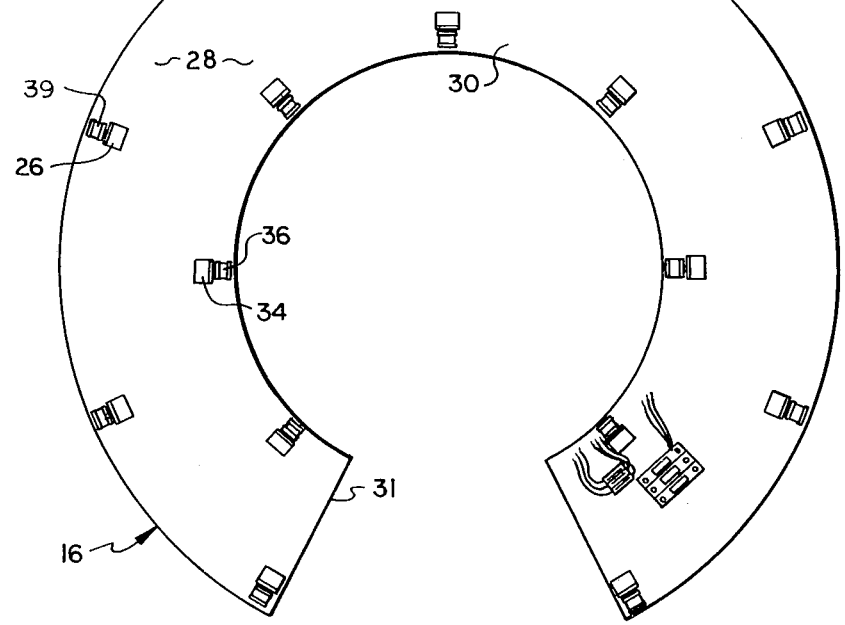
FIG. 6 is a top plan view of the main support base assembly of the revolving examination table apparatus of this invention.

As shown in FIG. 6, the basic table top member 22 is of a ring shape having a central opening 30 with entrance thereto gained through a cut-out section 31. The basic table top member 22 is formed with a motor cut-out section 32 for reasons to be explained. The upper support surface 28 extends in a horizontal plane and a plurality, namely, fourteen of the roller assemblies 26 are used.

Each roller assembly 26 includes an angle iron support member 34 secured to the basic table top member 22 and having a roller member 36 rotatably connected thereto on a shaft member 38. The roller members 36 rotate about a horizontal axis of the respective shaft members 38 to provide outer roller support surfaces 39 for reasons to be explained.

The revolving table top assembly 18 includes a main table top assembly 40 with a support track assembly 42 connected thereto. The main table top assembly 40 is of circular ring shape but having a seven sided central opening 44 to receive the optometrist therein. The main table top assembly 40 includes six (6) interconnected instrument table sections 46 and one pivotally connected entrance table section 48 movable from opened to closed and latched positions.

Each instrument table section 46 includes a main body member 50 integral with downwardly depending arcuate front wall 52, inclined sidewalls 54 and an inner wall 56. The adjacent sidewalls 54 of instrument table sections 46 are secured together as by nut and bolt members, rivet members, etc.

The entrance table section 48 is substantially identical to an instrument table section 46 except having (1) one sidewall 54 pivotally connected by a hinge member 58 to a sidewall 54 of an adjacent instrument table section 46 and (2) the area adjacent the other sidewall 54 has a latch assembly 60.

As shown in FIGS. 7 and 8, the latch assembly 60 includes (1) a rectangular support shell 62 mounted on an opening 64 in the main body member 50; and (2) an actuator handle assembly 66 connected to the support shell 62. The actuator handle assembly 66 includes (1) a handle member 68 pivotally mounted on a support shaft 70; and (2) a pair of lock pins 72 connected to the handle member 68 by linkage members 74. The support shaft 70 is connected to the support shell 62. The lock pins 72 are movable in guide holes 76 in the entrance table section 48 into pin receiving holes 77 in the adjacent instrument table section 46.

As shown in FIG. 8, the latch assembly 60 is in the latched position as shown in solid lines. The handle member 68 is pivoted to the position as shown in dotted lines to move the lock pins 72 as shown by the arrow 78 out of the pin receiving holes 77. The entrance table section 48 may then be moved to the open position as shown in FIG. 1.

Figure 4:
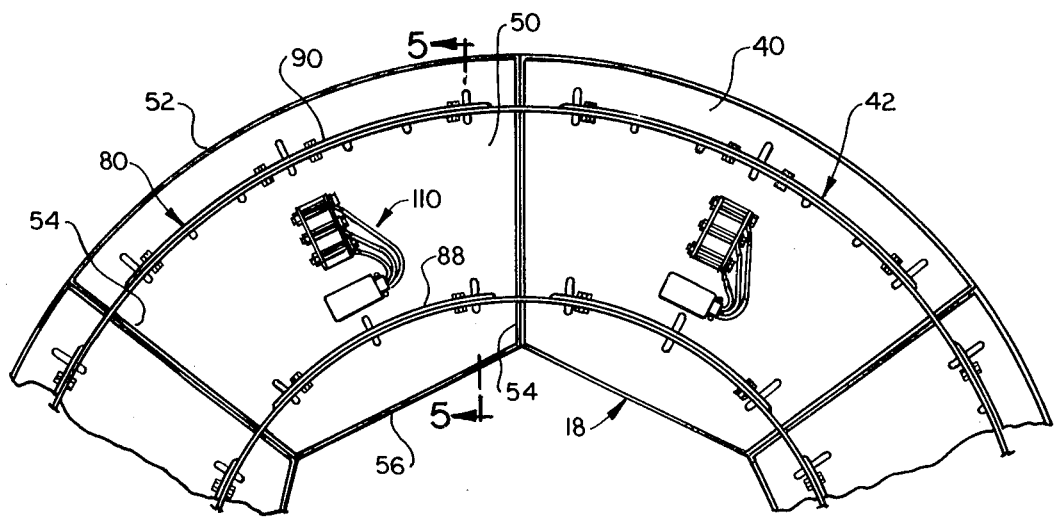
FIG. 4 is a fragmentary plan view of an undersurface of a revolving table top assembly of the revolving examination table apparatus of this invention.
Figure 5:
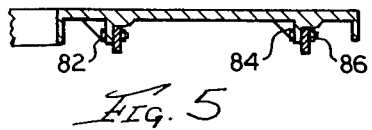
FIG. 5 is a fragmentary sectional view taken along line 5—5 in FIG. 4.

The support track assembly 42 includes a track assembly 80 secured to the undersurface of the main table top assembly 40 as by support assemblies 82 (FIGS. 4 and 5). Each support assembly 82 includes an anchor lug 84 connected to a portion of the track assembly 80 by a nut and bolt member 86.

The track assembly 80 includes an inner track member 88 and an outer track member 90, each of rectangular plate shape in transverse cross section (FIG. 5). The inner track member 88 and the outer track member 90 are of continuous circular shape except at the entrance table section 48 where they are short sections to allow opening of the entrance table section 48 as shown in FIG. 1.

It is obvious that the track assembly 80 is operable to be supported on the support surfaces 39 of the roller members 36 of the spaced roller assemblies 26 to permit rotation of the revolving table top assembly 18 in a manner to be explained.

The electrical control and drive assembly 20 includes (1) a table drive assembly 92 connected to the basic table top assembly 22; (2) a main power assembly 94; (3) a control panel assembly 96 and (4) an electrical control assembly 98.

As shown in FIG. 6, the table drive assembly 92 includes a drive motor member 101 connected through a gear box member 103 to drive wheel member 105. The drive wheel member 105 extends through the motor cut-out section 32 in the basic table top member 22 to contact the outer track member 90 of the track assembly 80 to rotate the revolving table top assembly 18 in a manner to be explained.

The main power assembly 94 includes (1) a stationary power contact assembly 107 secured to the upper support surface 28 of the basic table top member 22 at the home base working station indicated at 109; and (2) a plurality of receptacle power contact assemblies 110, each secured to one of the six (6) instrument table sections 46.

Figure 3:
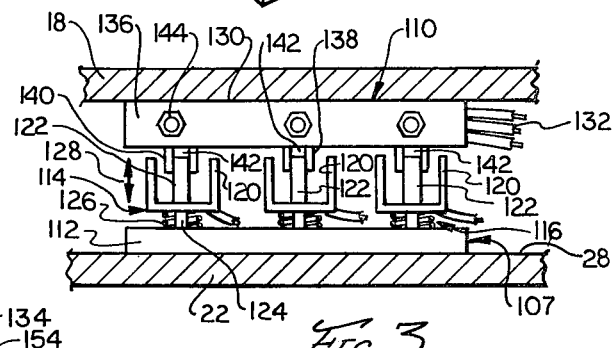
FIG. 3 is a fragmentary elevational view of a power assembly of the revolving examination table apparatus of this invention.

As shown in FIG. 3, the stationary power contact assembly 107 is positioned at the home base working station 109 and includes a support base member 112 and an electrical collector assembly 114 secured to the support base member 112 by a connector assembly 116. As noted in FIG. 2 the support base member 112 is secured to the basic table top member 22 as by bolt members 118.

The electrical collector assembly 114 includes three identical units, each having a U-shaped insulator body 120; a conductor member 122 mounted on the insulator body 120, and a wire member to connect the conductor member 112 to the control panel assembly 96 as will be explained. The conductor member 112 may be made of copper and shielded by the plastic insulator body 120.

The connector assembly 116 indicates (1) a bolt member 124 mounted on each end of the insulator body 120 and connected to the support base member 112; and (2) a compression spring 126 mounted about each bolt member 124 between the insulator body 120 and the support base member 112. By use of the compression spring 126, it is obvious that each unit of the electrical collector assembly 114 is movable as shown by an arrow 128 to assure electrical contact with the rotating receptacle power contact assemblies 110.

Each receptacle power contact assembly 110 includes a power conductor assembly 130 connected by electrical connector members 132 to a receptacle member 134. The power conductor assembly 130 includes a U-shaped support housing 136 having a conductor assembly 138 mounted thereon. The support housing 136 is secured to an undersurface of the revolving table top assembly 18.

The conductor assembly 138 has three identical units each having an insulated guide housing 140 with an electrical conductor member 142 mounted in the guide housing 140. The guide housings 140 are connected as by bolt members 144 to the support housing 136.

The electrical conductor members 142 are constructed of copper and operable to transfer electrical power from the stationary power contact assembly 107 through the electrical connector members 132 to the receptacle member 134.

The electrical connector members 142 include a ground wire member 146; a power wire member 148; and a safety ground wire member 150.

The receptacle member 134 is a conventional power outlet having a switch actuator or support housing 152; a lid member 154 mounted on the support housing 154; and an electrical receptacle 156 mounted in the support housing 152. The electrical receptacle 156 is connected to the electrical connector members 142 in a conventional manner to supply electrical power to an electrical plug 158 on the various instruments when in the home base working station 109.

As shown in FIG. 9, the control panel assembly 96 includes a suppot member 160 secured to the basic table top member 22 and having mounted thereon (1) an on-off switch 162; (2) a rheostat switch 164; (3) a table direction rotation switch 166; (4) an override switch 168 and (5) a power indicator light 170.

The electrical control assembly 98 includes a control switch assembly 172 mounted on the basic table top member 22 adjacent the stationary power contact assembly 107 (FIG. 2) and a circuit assembly 174 (FIG. 10).

The control switch assembly 172 includes three micro switches being (1) a normally closed motor power switch 176; and (2) a pair of normally open receptacle power switches 178 and 180 to provide power to the receptacle power contact assembly 110 in a manner to be explained.

Figure 2:
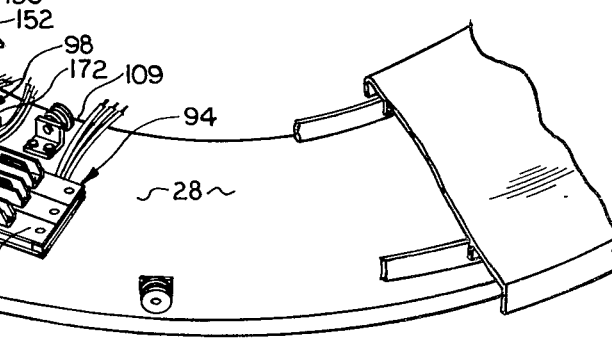
FIG. 2 is a fragmentary perspective view of the revolving examination table apparatus of this invention having portions broken away for clarity.

As shown in FIGS. 2 and 6, the three micro switches are secured to an upper surface 28 of the basic table top member 22. The micro switches are of a conventional nature, each having an actuator lever that is moved by the support housing 152 of the receptacle member 134. More particularly, the motor power switch 176 is opened and the receptacle power switches 178 and 180 are closed on contact of the support housing 152 with the actuator levers.

All reference to "wire" in the description of the circuit assembly 174 is understood to be conventional insulated electrical wire.

The circuit assembly 174 includes a plug-in member 182 connected to a power wire 184; a ground wire 186; and a safety ground wire 188. A circuit breaker 190 is mounted in the power wire 184 which is then connected to the rheostat switch 164 and through the receptacle power switch 178 and wire 189 to the conductor member 122 of the stationary power contact assembly 107.

The power indicator light 170 is connected by wires 190 and 192 between the power wire 184 and the ground wire 188 to indicate power available to the unit.

The ground wire 186 is (1) connected by a wire 194 to the rheostat switch 164; (2) connected by a wire 196 to the receptacle power switch 180 and then by wire 198 to the conductor member 122; and (3) connected by a wire 201 to the table rotation switch 166. A contact lever 203 in the table rotation switch 166 connects the wire 201 to either a wire 205 or a wire 207 connected to the drive motor member 101 to select direction of motor rotation. Simultaneously, a contact lever 209 in the table rotation switch 166 connects a wire 211 to the wire 207 in the condition of FIG. 10 and the wire 211 to the wire 205 in the other position to change direction of motor rotation. It is obvious that the contact levers 203 and 209 move conjointly as interconnected as shown by a dotted line 212. A motor rotation switch 166 is well known in the prior art.

The safety ground wire 188 is connected to the drive motor member 101 and connected by a wire 214 to the conductor member 122.

The rheostat switch 164 is of a conventional nature and varies the input voltage of 110 volts to an outlet wire 216 to control speed of rotation of the drive motor member 101. The outlet wire 216 is connected to the override switch 168 and, when the override switch 168 is closed, by a wire 218 to the drive motor member 101.

Also, the outlet wire 216 is connected to the on-off switch 162 which, in turn, is connected by a wire 220 to the normally closed motor power switch 176. The motor power switch 176 is connected to the wire 218 to the drive motor member 101.

It is seen that the receptacle power contact assembly 110 includes (1) the electrical conductor member 142 connected to the power wire member 148 to the receptacle member 134; (2) the electrical conductor member 142 connected to the safety ground wire member 150 to the receptacle member 134; and (3) the electrical conductor member 142 connected to the ground wire member 146 to the receptacle member 134.

USE AND OPERATION OF THE INVENTION

As shown in FIG. 1, the entrance table section 48 is pivoted to the open position when above the cut-out section 31 of the basic table top member 22. This permits an optometrist to enter the center of the revolving examination table apparatus 12 and utilize the stool 14 while examining a patient. The optometrist would face the home base working station 109 while the patient would be positioned on the outer, opposite side thereof.

The entrance table section 48 would be moved to the closed, horizontal position and secured by the latch assembly 60 to the adjacent instrument table section 46.

Next, the optometrist may select the speed of rotation of the revolving table top assembly 18 by setting the rheostat switch 164 as desired. The direction of rotation can be chosen by use of the table rotation switch 166.

Power is supplied to the control panel assembly 96 by plugging the plug 182 into a conventional electrical power receptacle and the power indicator light 170 would be energized. The on-off switch 162 is placed in the "ON" position. Nothing happens as the station power contact assembly 107 is in contact with the receptacle power contact assembly 110 and the receptacle member 134 actuates the control switch assembly 172 as shown in FIG. 10. Thus, the normally closed motor power switch 176 is opened and no power is supplied through wire 220 to wire 218 to the motor member 101.

To rotate the revolving table top assembly 18 to place an adjacent instrument table section 46 in the home base working station 109 position, the override switch 168, which is spring loaded, is depressed to supply power through wire 184, rheostat switch 164, wire 216, and wire 218 to the motor member 101.

After slight movement of the revolving table top assembly 18, the receptacle member 134 moves out of contact with the control switch assembly 172 to close the motor power switch 176. The override switch 168 is released and power is then supplied from wire 216, on-off switch 162, wire 220, motor power switch 176, and wire 218 to the motor member 101 to continue rotation of the revolving table top assembly 18.

On positioning the next instrument station at the home base working station 109, the next receptacle member 134 contacts the contact switch assembly 172 to open the motor power switch 176 and cease power to the motor member 101 to stop rotation of the revolving table top assembly 18. Simultaneously, the receptacle power switches 178 and 180 are closed to supply electrical power to the receptacle 134 having an instrument associated therewith now able to be energized.

This procedure may be repeated to move the revolving table top assembly 18 to the next instrument table section 46 by depressing the override switch 168 as described above and the procedure would be repeated.

Also, the operator may by-pass any instrument table section 46 by holding in the override switch 168 which will continue power to the motor member 101 through wires 216 and 218. On approaching a desired instrument table section 46, the override switch 168 is released and the automatic stopping of the revolving table top assembly 18 will take place.

The revolving examination table apparatus is very useful as permits the optometrist and the patient to remain in one position and rotate the necessary examination instruments to the home base working station. The revolving examination table apparatus is durable in construction, reliable in operation, and easy to use.

While the invention has been described in conjunction with preferred specific embodiments thereof, it will be understood that this description is intended to illustrate and not to limit the scope of the invention, which is defined by the following claims.

I claim:

1. A revolving examination table apparatus operable to selectively place examination instruments between an optometrist and his patient, comprising:
   (a) a main support base assembly includes a ring shaped basic table top member mounted on support leg members;
   (b) a revolving table top assembly having a main table top assembly rotatably mounted on said basic table top member;
   (c) each of said basic table top member and said main table top assembly having a central opening to receive the optometrist therein;
   (d) said main table top assembly rotates through an entire 360 degrees and includes a plurality of instrument table sections each adapted to support an examination instrument thereon;
   (e) an electrical control and drive assembly includes (1) a table drive assembly secured to said basic table top member and engagable with said main table top assembly to rotate same; (2) a power assembly having a stationary power contact assembly secured to said basic table top member at a home base working station and a receptacle power contact assembly having a receptacle member mounted at each instrument table section; (3) a control panel assembly secured to said basic table top member; and (4) an electrical control assembly having a control switch assembly mounted at said home base working station on said basic table top member and a circuit assembly to provide electrical power to said table drive assembly, said power assembly to energize separately a respective one of the said receptacle members, said control panel assembly, and said control switch assembly; and
   (f) said control panel assembly includes an override switch operable when actuated to rotate said revolving table top assembly and, when said override switch is released, the next one of said instrument table sections is automatically stopped at said home base working station.

2. A revolving examination table apparatus as described in claim 1, wherein:
   (a) when one of said instrument table sections is stopped at said home base working station, said stationary power contact assembly engages said receptacle power contact assembly to supply electrical power therebetween; and
   (b) said receptacle power contact assembly includes one of said receptacle members mounted on the top surface of each of said instrument table sections of said main table top assembly to supply power to an examination instrument at said home base working station.

3. A revolving examination table apparatus as described in claim 2, wherein:
   (a) said control switch assembly includes a pair of receptacle power switches to selectively supply power to said receptacle member and a motor power switch to selectively supply power to said table drive assembly.

4. A revolving examination table apparatus operable to selectively place examination instruments between an optometrist and his patient, comprising:
   (a) a main support base assembly includes a ring shaped basic table top member mounted on support leg members;
   (b) a revolving table top assembly having a main table top assembly rotatably mounted on said basic table top member;

(c) each of said basic table top member and said main table top assembly having a central opening to receive the optometrist therein;

(d) a main table top assembly includes a plurality of instrument table sections each adopted to support an examination instrument thereon;

(e) an electrical control and drive assembly includes (1) a table drive assembly secured to said basic table top member and engagable with said main table top assembly to rotate same; (2) a power assembly having a stationary power contact assembly secured to said basic table top member at a home base working station and a receptacle power contact assembly mounted at each instrument table section; (3) a control panel assembly secured to said basic table top member; and (4) an electrical control assembly having a control switch assembly mounted at said home base working station on said basic table top member and a circuit assembly to provide electrical power to said table drive assembly, said power assembly, said control panel assembly, and said control switch assembly;

(f) said control panel assembly includes an override switch operable when actuated to rotate said revolving table top assembly and, when said override switch is released, one of said instrument table sections is automatically stopped at said home base working station;

(g) when one of said instrument table sections is stopped at said home base working station, said stationary power contact assembly engages said receptacle power contact assembly to supply electrical power therebetween;

(h) said receptacle power contact assembly includes a receptacle member mounted on said main table top assembly to supply power to an examination instrument at said home base working station;

(i) said control switch assembly includes a pair of receptacle power switches to selectively supply power to said receptacle member and a motor power switch to selectively supply power to said table drive assembly; and (j) on rotation of said revolving table top assembly, said receptacle power contact assembly includes a switch actuator to engage said control switch assembly to (1) open said motor power switch and stop table rotation; and (2) close said receptacle power switches to supply said receptacle member at said home base working station.

5. A revolving examination table apparatus as described in claim 1, wherein:

(a) on rotation of said revolving table top assembly, said receptacle power contact assembly includes a switch actuator to engage said control switch assembly to automatically (1) open said motor power switch and stop table rotation; and (2) close said receptacle power switches to supply said receptacle member at said home base working station.

6. A revolving examination table apparatus operable to selectively place examination instruments between an optometrist and his patient, comprising:

(a) a main support base assembly includes a ring shaped basic table top member mounted on support leg members;

(b) a revolving table top assembly having a main table top assembly rotatably mounted on said basic table top member;

(c) each of said basic table top member and said main table top assembly having a central opening to receive the optometrist therein;

(d) said main table top assembly includes a plurality of instrument table sections each adapted to support an examination instrument thereon;

(e) an electrical control and drive assembly includes (1) a table drive assembly secured to said basic table top member and engagable with said main table top assembly to rotate same; (2) a power assembly having a stationary power contact assembly secured to said basic table top member at a home base working station and a receptacle power contact assembly mounted at each instrument table section; (3) a control panel assembly secured to said basic table top member; and (4) an electrical control assembly having a control switch assembly mounted at said home base working station on said basic table top member and a circuit assembly to provide electrical power to said table drive assembly, said power assembly, said control panel assembly, and said control switch assembly;

(f) said control panel assembly includes an override switch operable when actuated to rotate said revolving table top assembly and, when said override switch is released, one of said instrument table sections is automatically stopped at said home base working station;

(g) when one of said instrument table sections is stopped at said home base working station, said stationary power contact assembly engages said receptacle power contact assembly to supply electrical power therebetween; and (h) said receptacle power contact assembly includes a receptacle member mounted on the top surface of each of said instrument table sections of said main table top assembly to supply power to an examination instrument at said home base working station.

* * * * *